United States Patent [19]

Bille et al.

[11] Patent Number: 5,785,704

[45] Date of Patent: Jul. 28, 1998

[54] METHOD FOR PERFORMING STEREOTACTIC LASER SURGERY

[75] Inventors: Joseph F. Bille; Marcus H. Goetz. both of Heidelberg; Volker Sturm. Wiesloch-Schatthausen, all of Germany

[73] Assignee: MRC Systems GmbH, Heidelberg, Germany

[21] Appl. No.: 688,039

[22] Filed: Jul. 29, 1996

[51] Int. Cl.$^6$ .................................................. A61B 17/36
[52] U.S. Cl. ................................. 606/17; 606/14; 606/18; 606/130; 600/108
[58] Field of Search ........................... 606/7, 10–19, 606/130; 128/898; 607/88, 89; 600/108

[56] References Cited

U.S. PATENT DOCUMENTS

| | | |
|---|---|---|
| 3,653,743 | 4/1972 | Kiefer et al. |
| 3,693,623 | 9/1972 | Harte et al. |
| 4,388,924 | 6/1983 | Weissman et al. |
| 4,608,980 | 9/1986 | Aihara .................... 606/18 |
| 4,617,926 | 10/1986 | Sutton. |
| 4,638,800 | 1/1987 | Michel .................... 606/18 |
| 4,718,416 | 1/1988 | Nanaumi. |
| 4,754,328 | 6/1988 | Barath et al. .................... 606/17 |
| 4,887,605 | 12/1989 | Angelsen et al. .................... 606/18 |
| 4,998,930 | 3/1991 | Lundahl .................... 606/15 |
| 5,163,935 | 11/1992 | Black et al. .................... 606/17 |
| 5,298,026 | 3/1994 | Chang .................... 606/15 |
| 5,401,270 | 3/1995 | Muller et al. .................... 606/17 |
| 5,413,555 | 5/1995 | McMahan .................... 606/19 |
| 5,454,807 | 10/1995 | Lennox et al. .................... 606/17 |
| 5,496,307 | 3/1996 | Daikuzono .................... 606/17 |
| 5,558,670 | 9/1996 | Konwitz et al. .................... 606/18 |

*Primary Examiner*—Michael Peffley
*Attorney, Agent, or Firm*—Nydegger & Associates

[57] ABSTRACT

A method for the photodisruption of tissue using a laser beam for stereotactic laser neurosurgery includes the initial step of positioning the distal end of a probe into the tissue to be photodisrupted. A laser beam having laser pulses of picosecond or femtosecond duration is then directed along a beam path through the probe. Using a focusing lens, which is slidably positioned on the beam path in the probe, and a light reflector, which is slidably positioned on the beam path at the distal end of the probe, the laser beam is focused to a focal point that is located on a line substantially perpendicular to the beam path through the probe. By concerted movement of the lens and mirror, predetermined cylindrical layers of tissue can be photodisrupted. Specifically, a rotation of the mirror causes photodisruption of tissue along a circular arc and a simultaneous movement of the lens and mirror allows for photodisruption of additional arcs on a cylindrical surface. Further, by moving the lens relative to the mirror, cylindrical tissue surfaces having different radii can be photodisrupted. Additionally, the area of tissue photodisruption can be irrigated and aspirated during practice of the method.

38 Claims, 8 Drawing Sheets

METHOD FOR PERFORMING STEREOTACTIC LASER SURGERY

FIELD OF THE INVENTION

This invention is in the field of methods and apparatus used in the treatment of brain tumors and functional operations.

BACKGROUND OF THE INVENTION

The principle method currently in use for the treatment of brain tumors is the operative resection. Such treatment necessarily involves significant physical trauma to healthy surrounding tissues, especially when the tumor is deep-seated, located deep within the brain. Presently, the most prevalent treatment used in conjunction with the surgical resection is radiation therapy.

Radiation therapy typically is administered with the assistance of stereotaxis to achieve precise localization of the effects of the radiation in the tumor. Stereotaxis is accomplished with an external framework attached to the skull of the patient. Through these stereotactic methods, the radiation can be focused precisely on the tumor, to achieve a necrosis of the tumor tissue. If the volume of the tumor tissue is beyond a certain magnitude, the irradiation induced necrosis can have serious side effects. Irradiation induced necrosis can, in fact, grow like a tumor. In addition, fluid can accumulate at the site of the tumor, and the resulting edema can have long term effects, possibly even resulting in death. If chemotherapy is used in conjunction with the radiation therapy, the risks associated with irradiation induced necrosis are increased.

It is also currently known to treat brain tumors through laser surgery. Presently, the lasers used for this purpose are either a $CO_2$ laser or a Nd:YAG laser. Both of these lasers use thermal energy to vaporize or coagulate the tumor tissue. It happens, however, that the application of sufficient thermal energy to achieve tumor tissue necrosis through these mechanisms necessarily heats the surrounding tissues as well.

Current methods for laser surgery of brain tumors requires the laser be guided either manually or stereotactically. In either case, lengthy procedures are required. Currently used lasers must be focused on the tumor from a wide range of angles, so the treatment necessarily affects a relatively large volume of intervening tissue and requires an appreciable amount of time. Because tissue removal by currently used lasers is thermally induced, and because of the necessity for a wide range of approach angles, a considerable amount of heat expansion of surrounding healthy tissue occurs. The result is that the currently known methods of laser surgery are not a significant improvement over previously known surgical techniques.

SUMMARY OF THE PREFERRED EMBODIMENTS

The present invention is a method which improves the efficacy of laser surgery on brain tumors by using a type of laser which has a more effective tissue removal scheme, and by applying the laser beam from within the tumor to reduce the amount of surrounding healthy tissue that may otherwise be affected.

First, addressing the type of laser, a powerful solid state laser is used, with pulse durations in the one hundredth to one hundred picosecond range. The pulses from such a laser precisely break off small segments of tumor tissue, thereby eradicating the tumor by ablation, through a mechanism of non-thermal photodisruption of the tissue. There are no discernible effects in surrounding tissues.

Second, addressing the application of the laser from within the tumor, a laser probe has been devised which applies the laser energy at the precise location of the tumor, with a minimum amount of trauma to intervening tissues. The probe is sufficiently small to reach into a tumor with minimal trauma along the access path. Further, a single access path will often suffice, avoiding the wide range of approach angles necessitated by previously used laser equipment. The laser beam is emitted from a lateral opening at the distal end of the probe, perpendicular to the axis of the probe, or from a forward directed opening at the distal end of the probe, to strike a target within the tumor. The laser beam is then moved according to a planned sequence to progressively ablate tumor tissue until all of the tissue is removed.

The high power picosecond laser photodisrupts target tissue by an interaction mechanism called plasma-mediated ablation. Where specific ablation of localized tissue is desired, the laser is sharply focused on the tissue surface, creating a microplasma at the focus spot, where a high power density exists. The microplasma rapidly expands, generating a cavitation bubble and a shock wave. The cavitation bubble imposes stress on the tissue, and the shock wave creates a pressure gradient in the tissue, resulting in a mechanical disruption of the segment of tissue. In this way, the tumor tissue is fragmented into very fine particles. The energy level of the laser is controlled to achieve, but not greatly exceed, the ablation threshold. This results in ablation of the target tissue with negligible mechanical effects on surrounding tissue. Even at higher energies, the effects on surrounding tissues vanish within 300 microns of the focus spot.

The laser probe has a rigid tubular section and a mounting body which can be mounted on a head ring for stereotactic control purposes. The tubular section of the probe has a very small overall diameter, and it consists of three coaxial tubes. Other tube arrangements could also be used. The first, inner, tube provides a channel for the laser beam path, and it houses the necessary optical devices for control of the laser beam, including a focusing lens. The second tube surrounds the first tube, and a mirror is attached near the distal end of the second tube for deflecting the laser beam. A space between the first tube and the second tube provides a flowpath for irrigation fluid toward the distal end of the probe. The irrigation fluid is pumped down the space between the first tube and the second tube to clear the mirror and to put ablated tissue particles near the distal end of the probe into suspension. The third, outer, tube surrounds the first and second tubes, and a space between the second tube and the third tube provides a flowpath for aspirated irrigation fluid toward the proximal end of the probe. The aspirated fluid transports the suspended tissue particles and any accumulated biological fluid away from the operative area near the distal end of the probe. Therefore, as ablation occurs, continual irrigation and aspiration of the operative area removes the particles of tumor tissue as they are broken loose by ablation. The flow in the irrigation and aspiration flowpaths also can be controlled to regulate the intracranial pressure.

The mirror is located near the distal end of the probe. The laser beam passes longitudinally through the inner tube, toward the mirror at the distal end of the second tube. The mirror is angled so as to reflect the laser beam at approximately a ninety degree angle, causing the laser beam to exit the probe through a lateral opening in the tube, along a path approximately perpendicular to the longitudinal axis of the probe. The second tube, to which the mirror is attached, is movable longitudinally, both proximally and distally, to cause the laser beam exit point to move longitudinally along the probe.

The focusing lens is situated within the inner tube proximal to the mirror. The placement of the focusing lens relative to the mirror is accurately controlled by movement of the inner tube relative to the second tube so as to precisely focus the laser beam at a selected distance away from the axis of the probe. The selected distance is chosen to place the focus point on the surface of the tumor tissue to be ablated. The first and second tubes also can be moved in concert to maintain a desired focal distance while moving the exit path of the laser beam longitudinally.

The second tube can be rotated, to cause the mirror and the exit laser beam to rotate through a selected angle. The angle through which the mirror and laser beam are rotated can be any angle up to 360 degrees. Since the laser beam is focused at a point external to the probe, the focus point passes through an arc as the mirror rotates through the selected angle. If desired, the arc can form a full circle.

In addition to rotational movement, as mentioned above, the mirror and the focusing lens can be moved in concert along the longitudinal axis of the probe in either the distal or the proximal direction. During this movement, the distance between the mirror and the lens can be maintained precisely constant to insure that the perpendicular distance of the focus point from the probe axis remains constant. This longitudinal movement can be accomplished by simultaneous movement of the first and second tubes. As the mirror and lens are moved longitudinally, the position of the focus point also moves longitudinally, maintaining its selected distance from the probe axis.

If the longitudinal movement of the mirror and the lens is combined with the aforementioned full circle rotation of the mirror, the focus point will follow a spiral path generating a cylinder, coaxial with the probe. Rather than generating a full cylinder, a portion of a cylinder could be described by reciprocating rotation of the mirror through a lesser arc, simultaneous with the longitudinal movement of the mirror and lens.

Alternatively, rather than simultaneous rotation and longitudinal movement, the mirror could be rotated through a desired arc while the longitudinal position is held stationary, followed by an incremental longitudinal movement of the mirror and lens and a subsequent rotation of the mirror. This stepwise scheme could also be used to generate a partial or full cylinder. It can easily be seen that combinations of mirror rotation and longitudinal movement can be devised to cause the focus point to follow any portion of a cylindrical path along the surface of the target tissue, ablating a layer of tissue as it moves.

After movement of the focus point to follow a cylindrical path, as described above, the distance between the mirror and the focusing lens can be slightly decreased by moving the inner tube distally, to increase the perpendicular distance of the focus point from the probe axis. This new distance can be selected to place the focus point on the newly exposed surface of the tumor tissue remaining after removal of the first cylindrical layer of tissue by the ablation of tissue at the moving focus point.

As an example, the distal end of the probe can be initially inserted into the center of the tumor, thereby creating a cylindrical cavity in the center of the tumor, occupied by the probe. The focusing lens can then be moved to locate the focus point near the surface of the probe, focusing the laser beam on the adjacent surface of the tumor tissue. Longitudinal and rotational movement of the focus point can then ablate a generally cylindrical layer of tissue passing through the center of the tumor. To support the beginning of the procedure, a small balloon catheter, attached to the tip of the laser probe can slightly shift outwards the first layer of tissue. The ablated tissue fragments are then removed by aspiration through the probe, along with the irrigation fluid. Adjustment of the focus point to a location slightly farther from the probe axis, followed by repetition of the longitudinal and rotational movement, will result in ablation of a second cylindrical layer of tumor tissue. This process can be repeated until the tumor has been completely ablated and removed, from the center outwardly.

As a variation on the method, a layer of tumor tissue can be ablated from an irregular surface by adjustment of the perpendicular distance to the focus point simultaneously with longitudinal and rotational movement of the mirror. This allows the focus point, and hence the ablation point, to follow an irregular surface of tumor tissue, rather than being restricted to a cylindrical surface. This can be important when the outer layers of the tumor are ablated, since the tumor will seldom be cylindrically shaped. Thus, the outer layers of the tumor can be photodisrupted and removed without trauma to the surrounding healthy tissue.

During the performance of the laser surgery, it will often be necessary to coagulate blood vessels to avoid or control bleeding. This can be accomplished by defocusing the laser beam and then using the beam to heat the blood at the vessel location. A second laser, like a continuous wave laser which is capable of coagulating tissue, can also be used. In either case, this calls for visual monitoring of the operative area during the surgery, to locate and identify the blood vessels as they are exposed.

Further, in making this identification, it is very helpful to have specific information available to the surgeon, as to the location, size, and shape of such vessels, as well as other information about the tumor. Such information can be obtained pre-operatively through techniques such as X-ray computer tomography (CT) and magnetic resonance (MR) imaging. The visual monitoring in real time can be accomplished with a confocal laser scanning microscope connected to the laser probe. The real time image from the microscope can be matched to the previously obtained CT and MR information to facilitate accurate control of the operation. A computer can be programmed to follow a selected ablation path, or the probe can be directed manually by entry of computer commands in real time. In this way, a three dimensional plan can be devised for the surgery, and the plan can be stereotactically controlled by a combination of manual and computer control.

Real time monitoring with the laser scanning microscope can be enhanced with a laser doppler flowmeter to detect details such as individual capillaries which are too small to be seen visually. In addition, ultrasound can be used to detect larger vessels. Further, a fluorescence spectrometer can be integrated into the laser probe to identify and differentiate between tumor tissue and healthy tissue. In addition, ultrasound can be used to visualize the tumor borders on a macroscopic scale.

The novel features of the method of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
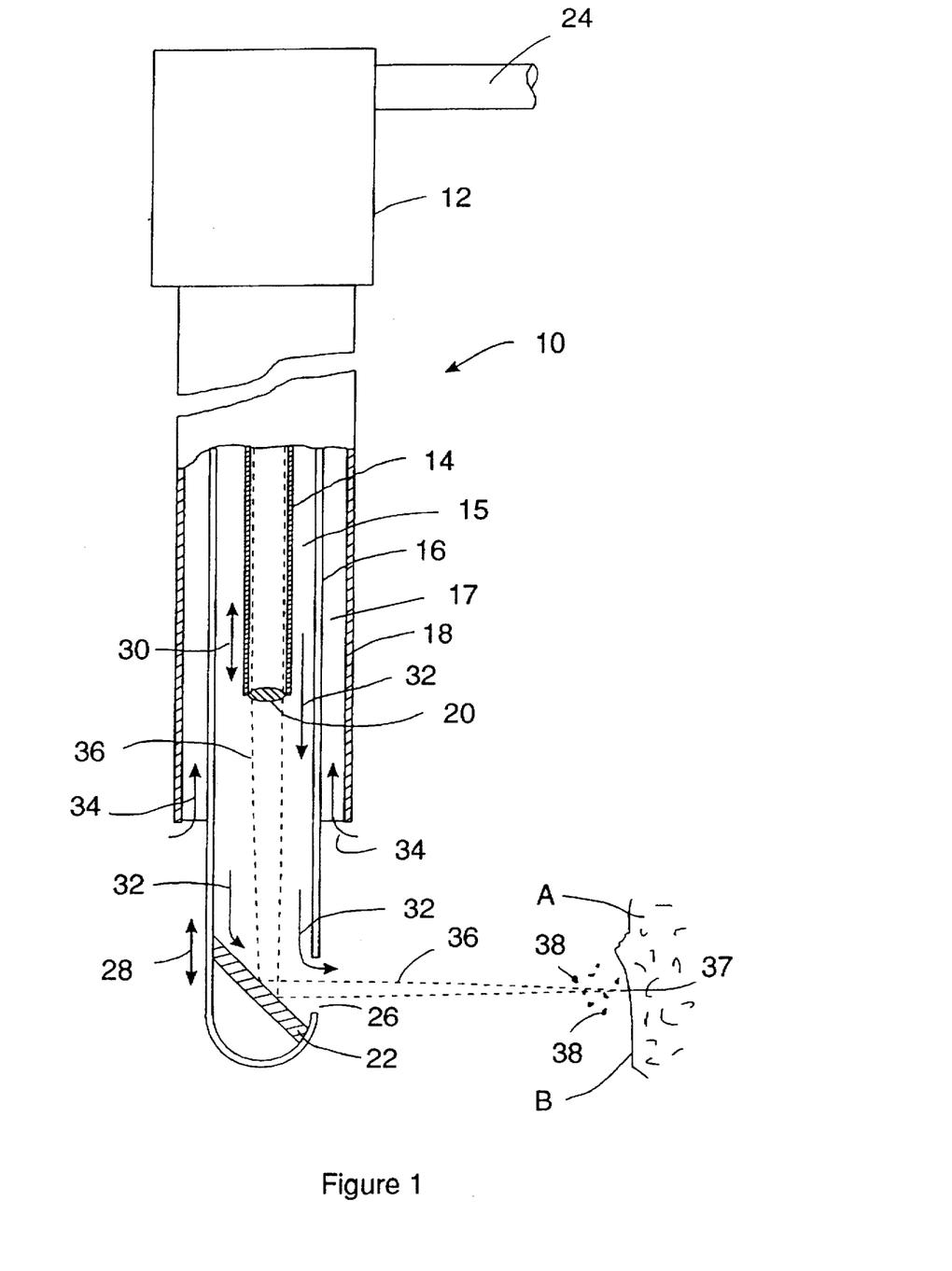
FIG. 1 is a partial section view of a laser probe for use in the method of the present invention.

Prior to description of the method of the present invention, it will be helpful to describe briefly an embodiment of the equipment which can be used in performing the method. As seen in FIG. 1, a laser probe 10 applies the laser energy at a precise location within the tumor A. The tubular distal portion of the probe 10 has a diameter of approximately 5.5 millimeters, and it is sufficiently small to reach into a tumor A with minimal trauma along the access path. The length of the tubular portion of the probe 10 is about 10 centimeters. The laser beam 36 is emitted laterally from the distal end of the probe 10, perpendicular to the axis of the probe 10, to strike the target surface B within the interior of the tumor A. Focusing of the laser beam 36 on to the surface B ablates the surface tissue by photodisruption to create loose tissue fragments or particles 38.

The distal portion of the laser probe 10 is a rigid tubular section consisting of three coaxial hollow tubes 14, 16, 18. Other tube arrangements could also be used. The coaxial tubes 14, 16, 18 are mounted to a mounting body 12. The first, inner, tube 14 provides a channel for the laser beam path, and it houses the necessary optical devices for control of the laser beam 36, including a focusing lens 20. The second tube 16 coaxially surrounds the first tube 14, and a mirror 22 is attached near the distal end of the second tube 16 for deflecting the laser beam 36. The laser beam 36 is represented pictorially in the figure as two rays for illustration purposes only.

A space 15 between the first tube 14 and the second tube 16 provides a flowpath 32 for irrigation fluid toward the distal end of the probe 10. An isotonic natrium chloride solution has been found suitable as an irrigation fluid. The irrigation fluid is pumped down the space 15 between the first tube 14 and the second tube 16 to clear the mirror 22 and to put ablated tissue particles 38 into suspension near the distal end of the probe 10. The third, outer, tube 18 surrounds the first and second tubes 14, 16. A space 17 between the second tube 16 and the third tube 18 provides a flowpath 34 for aspirated irrigation fluid toward the proximal end of the probe 10. The aspirated fluid transports the suspended tissue particles 38 and any accumulated biological fluid away from the operative area near the distal end of the probe 10. Therefore, as ablation occurs, continual irrigation and aspiration of the operative area removes the particles 38 of tumor tissue as they are broken loose from the surface B by ablation. The irrigation and aspiration flowpaths 32, 34 can be controlled by currently well known means to regulate the intracranial pressure at a selected level. A conduit 24 attached to the probe mounting body 12 can carry the laser beam 36 from the laser to the probe 10. Other connections to the mounting body 12 can be made for the irrigation fluid, the aspirated fluid, and any imaging or diagnostic equipment.

The mirror 22 is located near the distal end of the probe 10. The laser beam 36 passes longitudinally through the inner tube 14, toward the mirror 22 at the distal end of the second tube 16. The mirror 22 is angled so as to reflect the laser beam 36 at approximately a ninety degree angle, causing the laser beam 36 to exit the probe 10 through a lateral opening 26 in the second tube 16, along a path approximately perpendicular to the longitudinal axis of the probe 10. The second tube 16, to which the mirror 22 is attached, is movable longitudinally as indicated by arrow 28, both proximally and distally, to cause the exit point of the laser beam 36 to move longitudinally parallel to the axis of the probe 10. Longitudinal movement of the second tube 16 is accomplished by gearing or other mechanisms known in the art, located within the mounting body 12.

The focusing lens 20 is situated within the inner tube 14 proximal to the mirror 22. The placement of the focusing lens 20 relative to the mirror 22 is accurately controlled by longitudinal movement of the inner tube 14, as indicated by the arrow 30 so as to precisely focus the laser beam 36 at a selected distance away from the axis of the probe 10. The selected distance is chosen to place the focus point 37 on the exposed surface B of the tumor tissue to be ablated. Longitudinal movement of the inner tube 14 is also accomplished by gearing or other mechanisms known in the art, located within the mounting body 12. The first and second tubes 14, 16 also can be moved in concert to maintain a constant desired focal distance while moving the exit path of the laser beam longitudinally.

The second tube 16 can be rotated, to cause the mirror and the exit laser beam to rotate through a selected angle. Rotation of the second tube 16 is accomplished by gearing or other mechanisms known in the art, located within the mounting body 12. The angle through which the mirror 22 and the laser beam 36 are rotated can be any angle up to 360 degrees. Since the laser beam 36 is focused at a point 37 external to the probe 10, the focus point 37 passes through an arc as the mirror 22 rotates through the selected angle. If desired, the arc can form a full circle.

A powerful solid state laser is used to generate the laser beam 36, with pulse durations in the one hundredth to one hundred picosecond range. Taking into account the absorption losses in the irrigation fluid, the focal length of the laser is chosen to achieve an energy density at the tissue surface B of about 50 Joules per square centimeter. The ablation depth of a single laser pulse from such a laser is about 100 micrometers. The ablation area of such a pulse is about 100 micrometers by 100 micrometers. The pulses from such a laser precisely break off small segments of tumor tissue, thereby eradicating the tumor by ablation, through a mechanism of non-thermal photodisruption of the tissue. There are no discernible effects in surrounding tissues.

The high power picosecond laser photodisrupts target tissue by an interaction mechanism called plasma-mediated ablation. Where specific ablation of localized tissue is desired, as at the surface B of the tumor tissue, the laser is sharply focused on the tissue surface, creating a microplasma at the focus spot 37 where a high power density exists. The microplasma rapidly expands, generating a cavitation bubble and a shock wave. The cavitation bubble imposes stress on the tissue, and the shock wave creates a pressure gradient in the tissue, resulting in a mechanical disruption of the segment of tissue. In this way, the tumor tissue is broken into very fine fragments 38. The energy level of the laser is controlled to achieve, but not greatly exceed, the ablation threshold. This results in ablation of the target tissue with negligible mechanical effects on surrounding tissue. Even at higher energies, the effects on surrounding tissues vanish within 300 micrometers of the focus spot 37.

Figure 2:
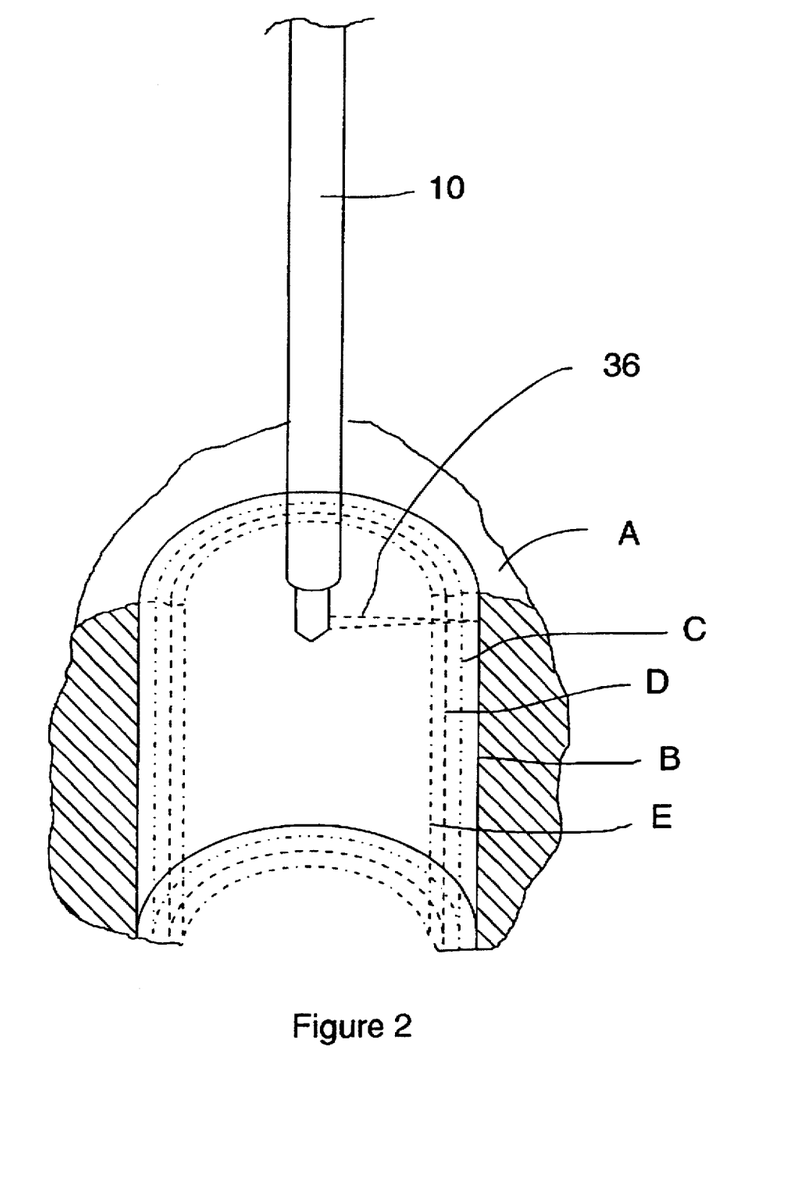
FIG. 2 is a partial section view of a tumor, showing a typical cylindrical tissue removal scheme.

FIG. 2 shows a section view of a tumor A, with the probe 10 inserted into the tumor A. The probe 10 is progressively ablating cylindrical layers C, D, E of tumor tissue from the surface B. The laser beam 36 is shown in the process of ablating a cylindrical layer C from the surface B, simultaneously moving in a proximal direction through the tumor A, while rotating through a full circle. The dashed lines illustrate the layer C currently being removed, along with the previously removed layer D, and the layer E which was removed before removal of layer D. It should be understood that other layers between the probe 10 and the layer E would have been removed prior to the removal of layer E, but they are not shown, in the interest of clarity of the drawing.

Figure 3:
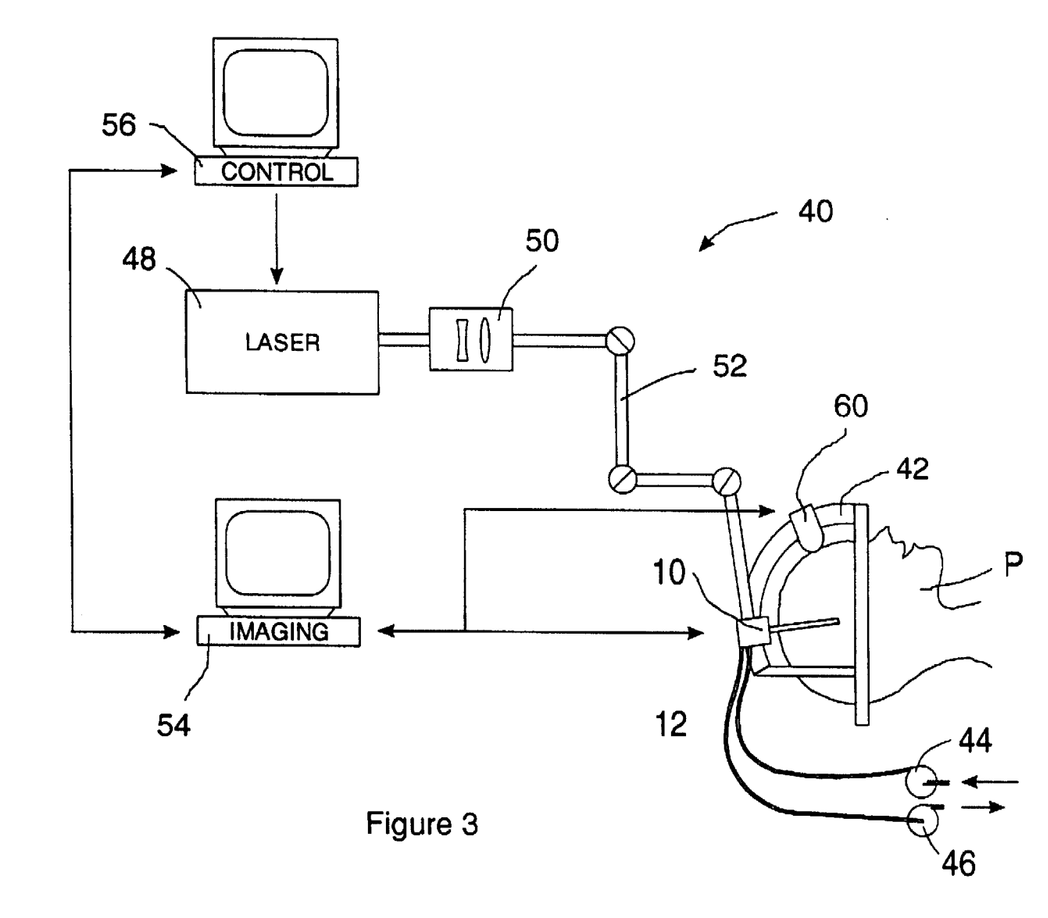
FIG. 3 a schematic of the apparatus used in performing the method of the present invention.

FIG. 3 shows other equipment comprising the imaging and control system 40 in which the laser probe 10 is used. The laser probe 10 is shown inserted into the cranium of the patient P. The laser probe 10 is mounted by means of the mounting body 12 on a head ring 42 as known in the art, for stereotactic control of the positioning of the laser probe 10. A source 44 of irrigation fluid and an aspiration means 46 are connected to the mounting body 12 of the laser probe 10. A high power solid state picosecond laser 48 is also connected to the mounting body 12 via beam guiding optics 50 and a flexible mirror system 52. An imaging device 54 and a control microprocessor 56 are also connected to the probe 10 and the head ring 42.

The imaging device 54 can be a laser scanning microscope, a laser doppler flowmeter, or a fluorescence spectrometer, or combinations thereof. Viewpaths for these devices can be established through the probe 10 by the use of fiber optics or other means. The real time imaging can be completed by ultrasound by means of a stereotactic guided ultrasound probe 60. The imaging device 54 can also have provision for the input of CT or MR image data, allowing the comparison of the real time image with the CT or MR image. The control microprocessor 56 controls the movement of the probe 10 via the head ring 42 and the movement of the tubes 14 and 16 of the probe 10. The control microprocessor 56 also controls the imaging device 54 and the laser 48. Mapping of the ablation scheme can be programmed into the control microprocessor 56, using image data obtained from ultrasound, CT, and MR devices. Manual control of the ablation process can be accomplished by entry of commands into the control microprocessor 56 while viewing the operative area in real time.

Figure 4:
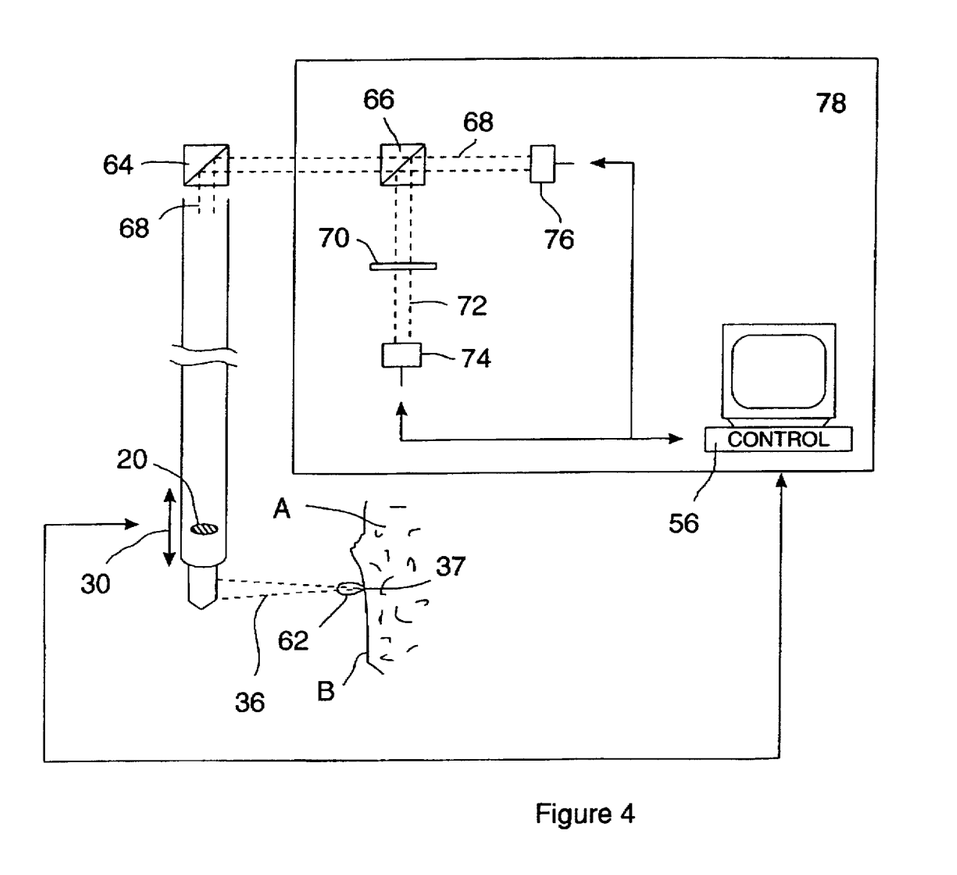
FIG. 4 is a schematic of the system components used for adjusting the position of the focusing lens to focus the laser onto a tissue layer.

FIG. 4 shows elements of the system which can be used to adjust the position of the focusing lens 20 of the probe 10 in a way that ensures the focus spot 37 hits the current tissue surface B inside the tumor A. To do this, the light beam 68 of the plasma spark 62 is reflected into the detection unit 78 by means of a beam splitter 64. The light beam 68 is further split into two arms by means of a second beam splitter 66. In the first arm, the total intensity of beam 68 is detected by the photodetector 76. In the second arm, wavelengths, capable of distinguishing between plasma light emitted from tissue and plasma light emitted from rinsing liquid, are separated and detected by means of spectral filters 70 and the photodetector 74. This arrangement allows for a comparison of the separated wavelengths and gives information whether the focus spot 37 lies before, on, or behind the tissue surface B. further this information can be put into the control microprocessor 56 to accurately position the laser beam 36.

Figure 5:
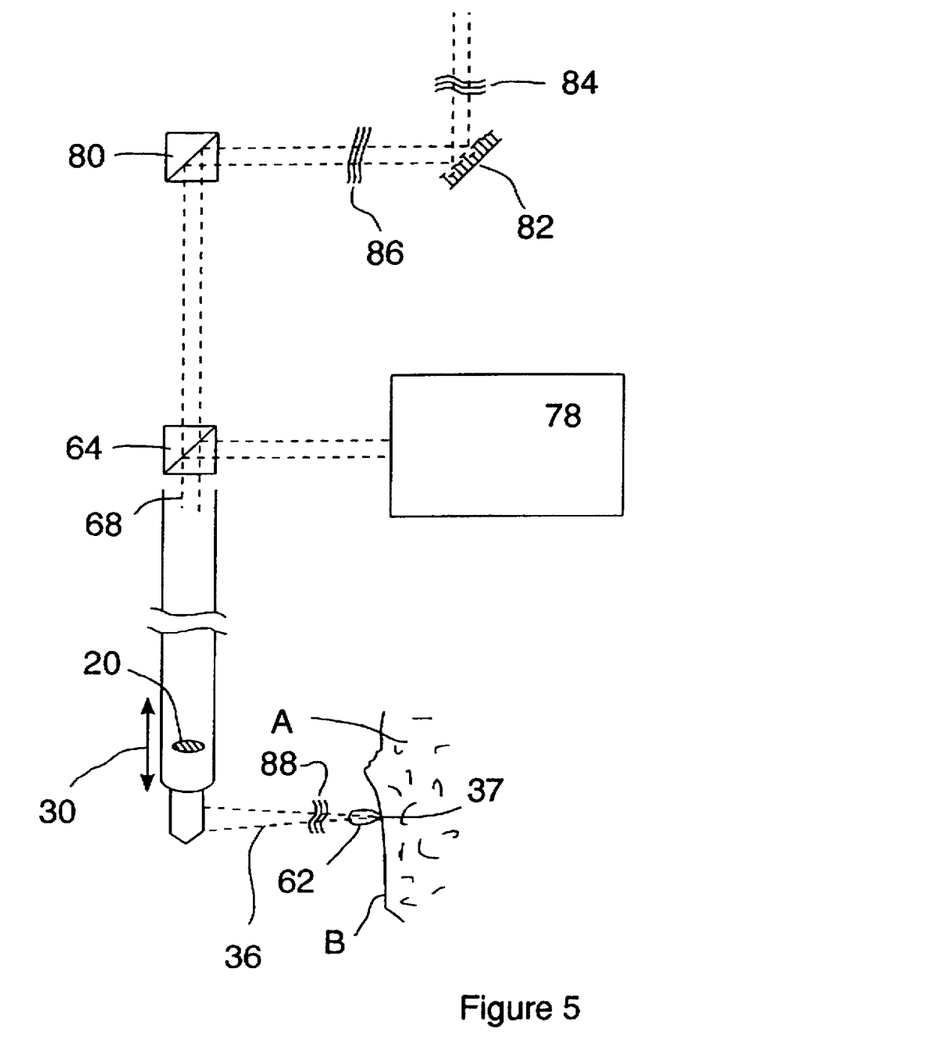
FIG. 5 is a schematic showing use of an active mirror to accomplish active-optical focusing.

FIG. 5 shows the method and apparatus to actively control the waveform and thereby the focus of the cutting laser beam 36 by means of an active-optical mirror 82. The single elements of the active-optical mirror 82 can be adjusted in a way known in the art, such that the distorted wavefront 84 of the cutting laser beam 36 can be orchestrated to achieve an optimized wavefront 88 near the tissue surface leading to a sharp focus spot 37. For purposes of the present invention an active optical mirror can be used of a type as described in J. F. Bille, A. W. Dreher, G. Zinser "Scanning Laser Tomography of the Living Human Eye" in "Noninvasive Diagnostic Techniques in Ophthalmology", ed. By B. R. Masters, Springer-Verlag (1990). The waveform 86 after the active-optical mirror is adjusted to compensate for aberrations of the laser light beam at the target.

Figure 6:
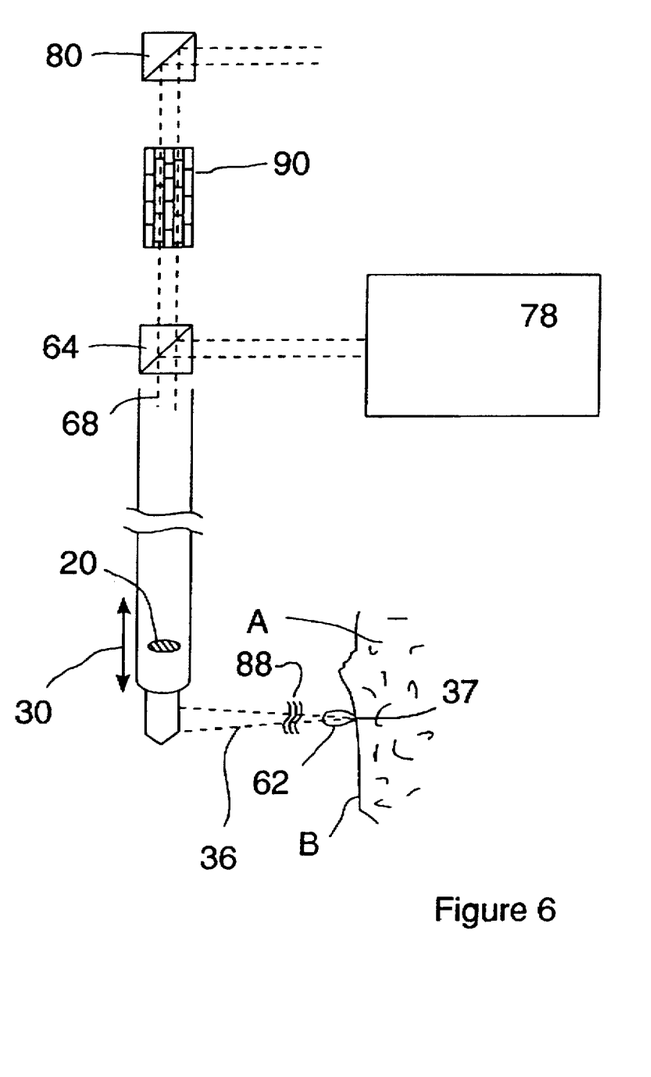
FIG. 6 is a schematic showing use of a liquid crystal light valve (LCLV) to accomplish active-optical focusing.

As shown in FIG. 6 a liquid crystal light valve (LCLV) 90 can be used instead of an active-optical mirror to accomplish the same results. According to the present invention the LCLV 90 can be a spatial light modulator (SLM) such as a LCLV as for example hex 69 spatial light modulator of Meadowlak Optics, New Jersey.

Figure 7:
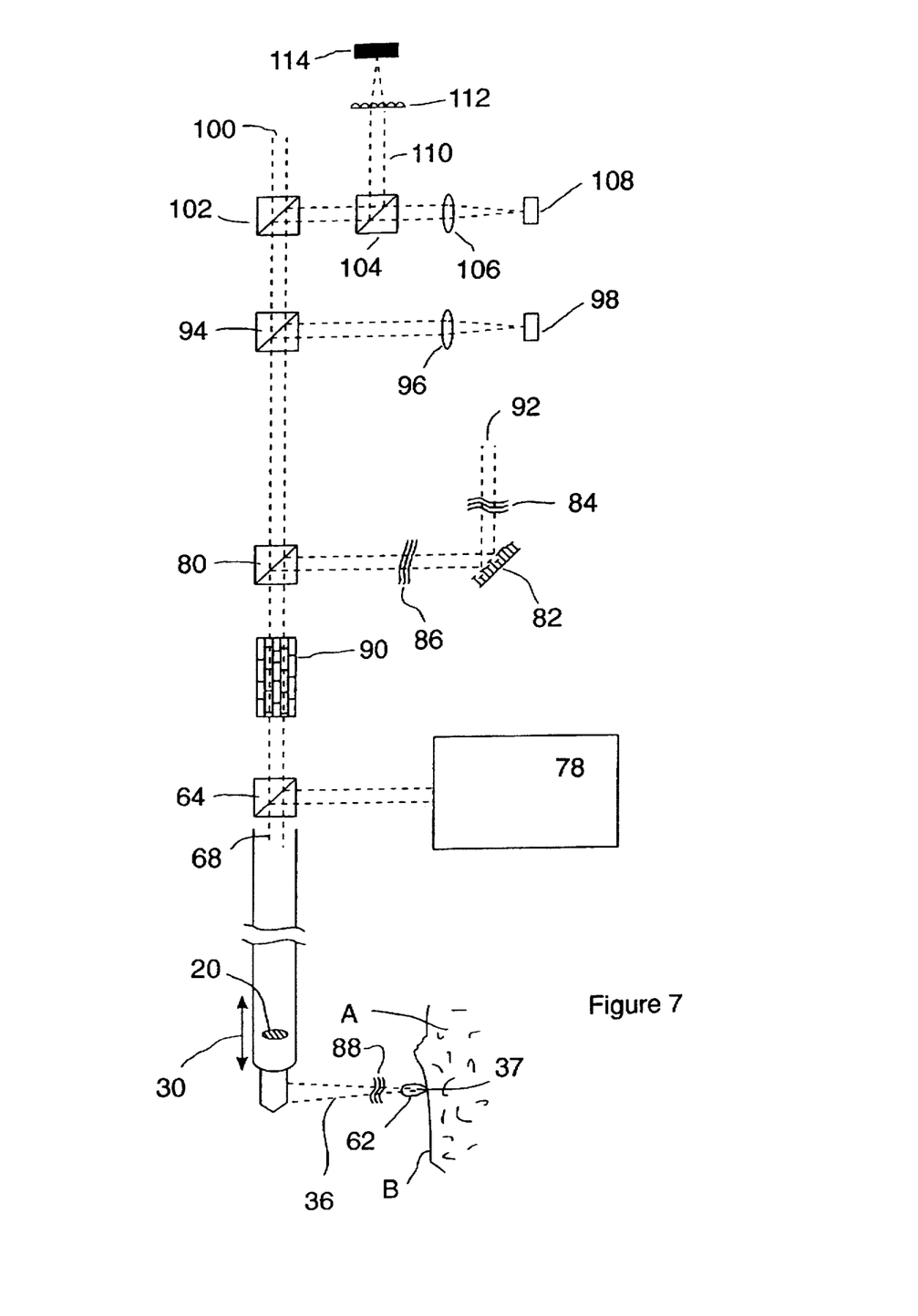
FIG. 7 is a schematic of the different subsystems used for the present invention to detect the light distribution of e focal spot response, the waveform of the cutting and or the pilot laser beam.

FIG. 7 illustrates two different methods to get information about the sharpness and quality of focus spot 37. First, a beam splitter 94 is used to separate a small fraction of the cutting laser light, which is reflected from the tissue surface. The light is imaged onto a diode array 98 by means of the lens 96. The diode array 98 measures the shape and thereby the sharpness of the focus spot 37. Second, a pilot beam 100, having a wavelength near to 670 nm, is reflected at the tissue surface B and is used to detect the quality of the focusing means. The quality of the focus spot can be measured either by imaging it onto the diode array 108 by means of the lens 106, and/or by separating the light beam using the beam splitter 104 and measuring the waveform by means of a Hartmann-Schack sensor where the beam 110 is imaged by the lens array 112 onto the CCD 114. These methods are all characterized in that the measured intensity distribution in a plane conjugate to the focal plane of the cutting beam and/or the pilot beam is compared to an ideal intensity distribution and control signals are derived for controlling the active mirror resp. the SLM to compensate for imaging errors.

Further, they are characterized in that the waveform of the pilot beam is measured by a wavefront sensor, e.g., a Hartmann-Shack wavefront sensor as described in J. Liang, B. Grimm, S. Goelz, J. F. Bille "Objective measurement of the wave aberrations of the human eye by the use of a Hartmann-Shack wavefront sensor" J. Opt. Soc. Am. Vol. 11 Nr. 7, pp. 1949–1957 (1994), is compared to an ideal waveform and control signals are derived for controlling the active mirror resp. the SLM to compensate for imaging errors.

OPERATION

The brain is mapped through ultrasound, CT or MR techniques to locate the tumor A and to develop information about the size and shape of the tumor A, as well as information about the location, size, and shape of blood vessels. This information is fed into the imaging device 54 and the control microprocessor 56. The control microprocessor 56 is programmed to control the placement and movement of the probe 10, the orientation of the laser beam 36, and the pulsing of the laser 48, to ablate and remove the tumor tissue. This establishes a three dimensional laser treatment scheme for the particular tumor A.

The skull of the patient is prepared for insertion of the probe 10, and the probe 10 is inserted into the cranium and approximately into the center of the tumor A. The laser 48 is energized and selectively pulsed by the control microprocessor 56 according to the aforementioned ablation program. Simultaneously, the orientation of the laser beam 36 is controlled by the control microprocessor 56 through rotational movement of the second tube 16 and through longitudinal movement of the first and second tubes 14, 16, according to the ablation program. Similarly, the distance of the focus spot 37 from the probe 10 is controlled by the control microprocessor 56 through longitudinal movement of the first tube 14 relative to the second tube 16, according to the ablation program. As the tumor tissue is photodisrupted by ablation, the tissue breaks off in very small fragments 38.

The progress of the ablation process can be observed by the surgeon on a video monitor on the imaging device, through the confocal laser scanning microscope. The real time image can be enhanced with the laser doppler flowmeter or the fluorescence spectrometer. The laser doppler flowmeter detects frequency shifts in reflected light, through well known means, to identify tumor tissue or individual capillaries too small to be seen otherwise. In addition, ultrasound can be used to detect larger vessels. A signal representative of the real time image is compared with a signal representative of the CT or MR image. The error between the two signals can be electronically compared and minimized by the control microprocessor 56 to accurately position the laser beam 36.

The fluorescence spectrometer requires the staining of tissue with a dye. A dye such as Hematoporphyrin Derivate (HpD) can be injected into the operative area through well known means to enable the use of the fluorescence spectrometer in identifying tumor tissue as differentiated from healthy tissue. The intensity of the fluorescence can be measured to differentiate between tumor tissue and healthy tissue, according to well known procedures. Further, the time delay of emitted fluorescence can be measured to identify tumor tissue and healthy tissue, according to well known procedures. In addition, ultrasound can be used to visualize the tumor borders on a macroscopic scale.

Blood vessels can be located through the mapping techniques of CT and MR imaging through ultrasound imaging, visually through the laser scanning microscope, or through other means. When a blood vessel is encountered, the laser beam 36 can be defocused and used to heat the blood in the vessel to coagulate the blood, sealing the vessel. The blood vessel can also be coagulated by other means.

The control microprocessor 56 can control the orientation, movement, and pulsing of the laser beam 36 to ablate a cylindrical layer of tumor tissue. The irrigation source 44, such as a pump, provides a fluid such as an isotonic natrium chloride solution to the operative area. The aspiration means 46, such as a vacuum pump, aspirates the solution, along with any suspended particles and other debris, from the operative area to aspirate the tumor tissue fragments 38. After ablating a cylindrical layer, the focal distance can be increased to locate the focus spot on the newly exposed surface of tumor tissue. Repeated manipulation of the laser beam 36 then removes an additional layer of tumor tissue. The axial length of the cylinder which can be ablated depends upon the focal length of the laser beam 36, which depends upon the power output of the picosecond laser 48. A typical apparatus having a relatively limited laser power might be limited to an axial movement of the laser beam 36 of approximately 20 millimeters.

Figure 8:
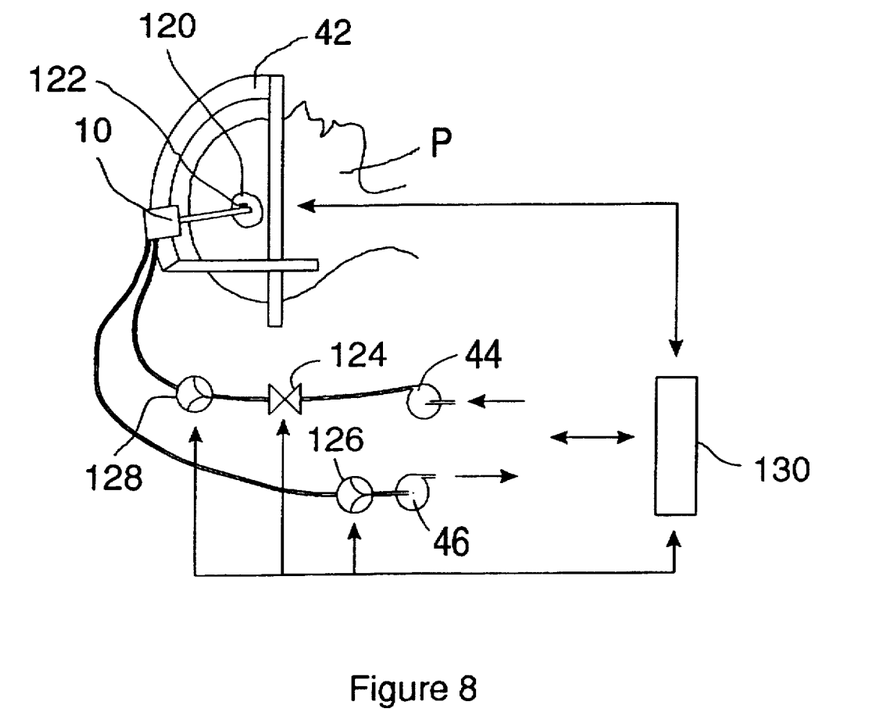
FIG. 8 is a schematic of the apparatus used in the present invention to control the intracranial pressure.

FIG. 8 shows the schematic of the arrangement used to control the intracranial pressure. A miniaturized pressure sensor 122 is attached to the tip of the probe and accurately measures the pressure within the ablation cavity 120. The signal is put into the microprocessor interface 130. By means of the pumps 44 and 46, and the valve 124 the flow of rinsing liquid can be controlled. The fluid can be measured by the flow meters 126 and 128, which measure the aspiration and irrigation, respectively. The signal of the flow meters is also put into the interface 130.

Using a picosecond laser with a pulse energy of 2.5 millijoules and a repetition rate of 4 kHz, the ablation velocity is approximately 4 cubic millimeters per second, or 15 cubic centimeters per hour. The desired power density at the surface of the tumor tissue is about 50 Joules per square centimeter.

The layers removed can be fully cylindrical as illustrated, or they can be partial cylinders. Further, they can have other shapes, according to the ablation scheme programmed into the control microprocessor 56.

While the particular METHOD FOR PERFORMING STEREOTACTIC LASER SURGERY as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for using a laser beam in stereotactic laser neurosurgery for the photodisruption of malignant tissue which comprises the steps of:

locating a hollow probe to establish extracorporeal access to the tissue to be photodisrupted, said hollow probe having a proximal end and a distal end and being formed with a channel;

selectively placing a light reflector near said distal end of said probe;

directing said laser beam on a beam path through said channel of said probe for reflection from said light reflector in a direction away from said beam path;

positioning a lens in said channel proximal to said light reflector to focus said laser beam at a desired focal point;

moving said light reflector, in concert with movement of said lens, to move said focal point in a predetermined manner for photodisruption of the tissue;

rinsing said light reflector with a solution; and aspirating said solution together with photodisrupted debris from around said tissue.

2. A method as recited in claim 1 wherein said moving step further comprises the steps of:

rotating said light reflector through an arc to photodisrupt tissue at a predetermined radial distance from said light reflector along said arc; and simultaneously moving said light reflector and said lens in a proximal/distal direction through an equal distance to photodisrupt tissue along successive arcs in said proximal/distal direction.

3. A method as recited in claim 2 wherein said arc is approximately three hundred and sixty degrees.

4. A method as recited in claim 3 wherein a range for movement in said proximal/distal direction is approximately twenty millimeters.

5. A method as recited in claim 4 further comprising the step of moving said lens in said proximal/distal direction relative to said light reflector to vary said radial distance of said focal point relative to said light reflector.

6. A method as recited in claim 5 wherein photodisruption of said tissue creates a plasma spade and said method further comprises the step of controlling the movement of said lens in said proximal distal direction relative to said light reflector, by detecting the light of the plasma spark to measure the position of said focal point relative to the current tissue surface.

7. A method as recited in claim 6 wherein said laser beam has a waveform and said method further comprises the step of controlling the waveform of the laser beam by an active mirror.

8. A method as recited in claim 7 further comprising a step of controlling the waveform of the laser beam by a spatial light modulator.

9. A method as recited in claim 6 further comprising the steps of:

measuring an intracranial pressure; and controlling the intracranial pressure on said tissue at a preselected level.

10. A method as recited in claim 1 wherein said laser beam has an energy density of approximately 50 J/cm$^2$.

11. A method as recited in claim 1 wherein said laser beam comprises a plurality of pulses having a pulse duration in the range of from one hundredth to one hundred picoseconds.

12. A method as recited in claim 11 wherein each said pulse in said laser beam has a pulse energy of approximately 2.5 mJ and a repetition rate for said pulses of said laser beam is approximately 4 kHz.

13. A method as recited in claim 1 further comprising the steps of:

delaying said moving step to fix said focal point at a position for a predetermined period of time; and defocusing said laser beam to coagulate blood at said position.

14. A method as recited in claim 13 further comprising the steps of:

identifying a blood vessel in the tissue to be photodisrupted; and performing said delaying step and said defocusing step on said blood vessel.

15. A method as recited in claim 14 wherein said identifying step is accomplished using a confocal laser scanning microscope for real time viewing of the tissue.

16. A method as recited in claim 14 wherein said identifying step is accomplished using a laser doppler flowmeter for real time viewing of the tissue.

17. A method as recited in claim 14 wherein said identifying step includes the steps of:

dying the tissue to be photodisrupted;

exciting the dyed tissue with a laser pulse having a fixed wavelength to create a fluorescent intensity; and measuring the fluorescent intensity of the tissue as an indication and identification of the tissue to be photodisrupted.

18. A method as recited in claim 17 wherein said dying step is accomplished using Hematoporphyrin Derivate (HpD).

19. A method as recited in claim 14 wherein said identifying step includes the steps of:

dying the tissue to be photodisrupted;

exciting the dyed tissue with a laser pulse having a fixed wavelength to generate a fluorescence in the tissue after a time delay; and measuring the time delay of fluorescence as an indication and identification of the tissue to be photodisrupted.

20. A method as recited in claim 19 wherein said dying step is accomplished using Hematoporphyrin Derivate (HpD).

21. A method as recited in claim 1 further comprising the steps of determining a boundary between the malignant tissue to be photodisrupted and healthy tissue.

22. A method as recited in claim 21 wherein said determining step is accomplished using ultrasound imaging for real time viewing of the tissue.

23. A method as recited in claim 21 wherein said determining step is accomplished using a confocal laser scanning microscope for real time viewing of the tissue.

24. A method as recited in claim 21 wherein said determining step is accomplished using a laser doppler flowmeter for real time viewing of the tissue.

25. A method as recited in claim 21 wherein said determining step includes the steps of:

dying the tissue to be photodisrupted;

exciting the dyed tissue with a laser pulse having a fixed wavelength to create a fluorescent intensity; and measuring the fluorescent intensity of the tissue as an indication and identification of the tissue to be photodisrupted.

26. A method as recited in claim 1 further comprising the steps of:

constructing a magnetic resonance image of the tissue to be photodisrupted;

viewing the tissue to be photodisrupted using a confocal laser scanning microscope to generate a real time image of the tissue to be photodisrupted;

and comparing said magnetic resonance image with said real time image to accomplish said directing step.

27. A method as recited in claim 1 further comprising the steps of:

constructing a magnetic resonance image of the tissue to be photodisrupted;

viewing the tissue to be photodisrupted using a laser doppler flowmeter to generate a real time image of the tissue to be photodisrupted; and comparing said magnetic resonance image with said real time image to accomplish said directing step.

28. A method as recited in claim 1 wherein said predetermined manner in said step of moving said mirror creates a separate piece of the tissue to be photodisrupted.

29. A method as recited in claim 1 further comprising the steps of:

constructing a magnetic resonance image of the tissue to be photodisrupted;

generating a first signal, said first signal being a characteristic of said magnetic resonance image;

viewing the tissue to be photodisrupted using a laser doppler flowmeter to generate a real time image of the tissue to be photodisrupted;

generating a second signal, said second signal being characteristic of said real time image;

comparing said first signal of said magnetic resonance image with said second signal of said real time image to create an error signal; and accomplishing said moving step to minimize said error signal.

30. A method as recited in claim 1 further comprising the steps of:

locating a balloon catheter near said distal end of said probe; and shifting outwards the tissue by inflating said balloon catheter.

31. A method as recited in claim 1 wherein said solution is isotonic natrium chloride.

32. A device for using a laser beam in stereotactic laser neurosurgery for the photodisruption of malignant tissue which comprises:

a hollow probe assembly formed with a channel and having a proximal end and a distal end;

a source of laser light connected in light communication with said proximal end of said probe to direct a beam of laser light through said channel from said proximal end toward said distal end;

a reflector slidably and rotatably mounted on said distal end of said probe for selectively directing said laser beam from said probe toward the malignant tissue;

a lens system for focusing said laser beam at a focal point on said malignant tissue distal from said reflector to generate photodisrupted debris;

irrigation means for rinsing said reflector with a solution; and aspiration means for aspirating said solution with said photodisrupted debris from said tissue.

33. A device as recited in claim 32 wherein said reflector is a mirror.

34. A device as recited in claim 32 wherein said reflector is a prism.

35. A device as recited in claim 32 wherein said lens system further comprises an active mirror for focusing said laser beam.

36. A device as recited in claim 32 wherein said lens system further comprises a liquid crystal light valve for focusing said laser beam.

37. A device as recited in claim 32 further comprising means for real time imaging of said malignant tissue, said real time imaging means being mounted in light communication with said channel of said probe via said proximal end thereof.

38. A device as recited in claim 37 wherein said means for real time imaging further comprises an ultrasonic probe.

* * * * *